United States Patent [19]
Kaplan

[11] 3,944,588
[45] Mar. 16, 1976

[54] CATALYTIC PROCESS FOR POLYHYDRIC ALCOHOLS AND DERIVATIVES

[75] Inventor: Leonard Kaplan, Charleston, W. Va.

[73] Assignee: Union Carbide Corporation, New York, N.Y.

[22] Filed: Jan. 2, 1975

[21] Appl. No.: 537,863

[52] U.S. Cl. ...... 260/449 L; 252/431 R; 252/431 N; 252/431 P; 252/431 L; 252/443; 260/485 G; 260/488 J; 260/449.5; 260/449 R
[51] Int. Cl.² ............... C07C 27/06; C07C 29/16
[58] Field of Search ......... 260/449 R, 449 L, 449.5; 252/431 R, 431 N, 431 P, 431 L, 443

[56] References Cited
UNITED STATES PATENTS

| | | | |
|---|---|---|---|
| 2,692,274 | 10/1954 | Kolbel et al. ............... | 260/449 L |
| 3,081,357 | 3/1963 | Alderson et al. ............. | 252/443 |
| 3,487,112 | 12/1919 | Paulik et al. ................ | 252/431 P |
| 3,560,539 | 2/1971 | Booth ........................ | 252/431 P |
| 3,576,881 | 4/1971 | Senn ......................... | 260/604 HF |
| 3,641,076 | 2/1972 | Booth ........................ | 252/431 P |
| 3,725,534 | 4/1973 | Reisch ....................... | 260/604 HF |
| 3,833,634 | 9/1974 | Pruett et al. ................ | 260/449 R |

FOREIGN PATENTS OR APPLICATIONS

| | | | |
|---|---|---|---|
| 793,086 | 6/1973 | Belgium ...................... | 260/449 |

OTHER PUBLICATIONS

Martineugo et al. Gazz., 102 (1972) 344-354.

*Primary Examiner*—Howard T. Mars
*Attorney, Agent, or Firm*—George A. Skoler

[57] ABSTRACT

This invention relates to the manufacture of such valuable chemicals as polyhydric alcohols, their ether and ester derivatives, oligomers of such alcohols and monohydric alcohols and their ether and ester derivatives by reacting hydrogen and oxides of carbon in the presence of a rhodium carbonyl complex and a trialkanolamine borate.

14 Claims, No Drawings

CATALYTIC PROCESS FOR POLYHYDRIC ALCOHOLS AND DERIVATIVES

This invention is concerned with the manufacture of polyhydric alcohols, their ether and ester derivatives, and oligomers of such alcohols. This invention also produces monohydric alcohols, such as methanol, and their ether and ester derivatives.

Polyhydric alcohols are presently being produced synthetically by the oxidation of petroleum derived materials. Owing to the limited availability of petroleum sources, the cost of these petroleum derived materials has been steadily increasing. Many have raised the dire prediction of a significant oil shortage in the future. The consequence of this has been the recognition of the need for a new low cost source of chemicals which can be converted into such polyhydric alcohols.

This invention is directed to the process of making polyhydric aliphatic alcohols, and to their ether, ester and oligomer derivatives. In particular, this invention is concerned with the diols and triols containing 2 or 3 carbon atoms, their ethers, ester and oligomer derivatives. A byproduct of this invention is the manufacture of the lesser valuable, but valuable nevertheless, monohydric alkanols such as methanol, ethanol and propanols, and their ether and ester derivatives. The products of the process of this invention contain carbon, hydrogen and oxygen.

There are described in U.S. Pat. 3,833,634, issued Sept. 3, 1974, and copending application Ser. No. 462,109, filed Apr. 18, 1974, processes for reacting hydrogen and oxides of carbon in the presence of rhodium carbonyl complex catalysts. One problem associated with these processes is preventing the loss of the catalyst during the reaction. Inasmuch as the rhodium used in the catalyst is an extremely expensive metal, having a current dealer's price of about $285. per troy ounce, it is particularly desirable to avoid any significant loss of such rhodium values during the course of the reaction.

In accordance with the practice of the present invention these losses of rhodium may be significantly reduced when the aforementioned reactions of hydrogen and oxides of carbon are conducted in the presence of a trialkanolamine borate.

The process of the present invention involves the production of alkane diols and triols having from 2 to 3 carbon atoms in the molecule by reacting in a suitable solvent a mixture of hydrogen and oxides of carbon in the presence of a rhodium carbonyl complex and a trialkanolamine borate.

Illustrative of the trialkanolamine borates useful in the practice of the present invention are those of the formula $B(OR)_3N$ wherein R is a straight or branched chain alkylene radical having from 1 to 14 carbon atoms, preferably 1 to 3 carbon atoms in the alkylene chain. These trialkanolamine borates may be prepared according to the methods disclosed in U.S. Pat. Nos. 3,103,531 and 2,785,192 and the articles Ind. Eng. Chemistry, 49, 174 (1957) and J. Am. Chem. Soc., 82, 853 (1960) both by Steinberg and Hunter.

The use of trialkanolamine borates of the formula:

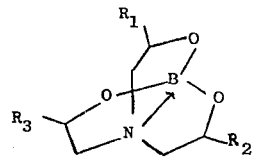

wherein $R_1$, $R_2$, and $R_3$ are at least one of hydrogen or lower alkyl, preferably methyl, represents a preferred embodiment of the present invention. Illustrative of these preferred borates are triethanolamine borate and triisopropanolamine borate.

The rhodium carbonyl complexes suitable for use in the practice of the present invention are those wherein the complex is at least one of (1) rhodium in complex combination with carbon monoxide, (2) rhodium in complex combination with carbon monoxide and hydrogen, (3) rhodium in complex combination with carbon monoxide and at least one Lewis base, (4) rhodium in complex combination with carbon monoxide, hydrogen and at least one Lewis base, and (5) mixtures thereof.

Moreover, the rhodium carbonyl complexes of this invention may be in the form of rhodium carbonyl clusters. P. Chini, in a review article entitled "The Closed Metal Carbonyl Clusters" published in Review (1968), Inorganica Chimica Acta, pages 30–50 states that a metal cluster compound is a "a finite group of metal atoms which are held together entirely, mainly, or at least to a significant extent, by bonds directly between the metal atoms even though some non-metal atoms may be associated intimately with the cluster". The rhodium carbonyl cluster compounds of this invention contain rhodium bonded to rhodium or rhodium bonded to another metal, such as cobalt, and/or iridium. The preferred rhodium carbonyl cluster compounds of this invention are those which contain rhodium-rhodium bonds. These compounds desirably contain carbon and oxygen in the form of carbonyl (—C—O), in which the carbonyl may be "terminal", "edge-bridging", and/or "face-bridging". They may also contain hydrogen and carbon in the froms other than carbonyl. The following are illustrative of what is believed to be the structure of two distinct rhodium carbonyl clusters and both are suitable for use in this invention.

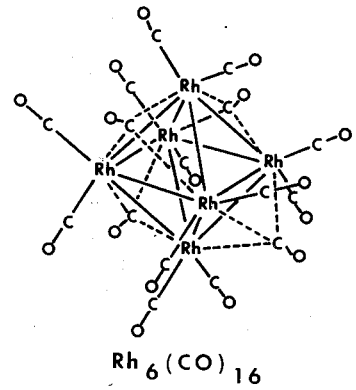

$Rh_6(CO)_{16}$

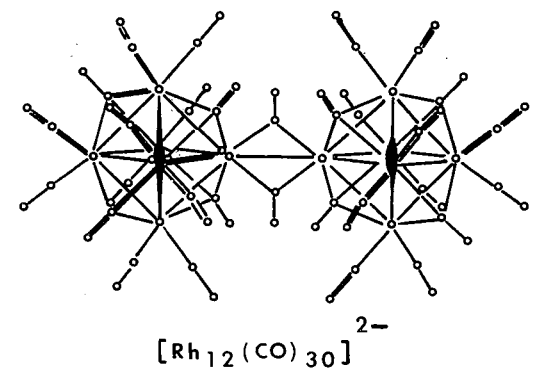

$[Rh_{12}(CO)_{30}]^{2-}$

The structures of the rhodium carbonyl clusters may be ascertained by X-ray crystal diffraction, nuclear magnetic resonance spectra (NMR), or infrared spectra as disclosed in the article entitled "Synthesis and Properties of the Derivatives of the $[Rh_{12}(CO)_{30}]^{2-}$ Anion" by P. Chini and S. Martinengo; appearing in Inorganica Chimica Acta, 3:2 pp.299–302, June (1969). Of particular analytical utility in the present invention is the use of infrared spectroscopy which allows for characterization of the particular rhodium carbonyl complex present during the operation of the process of the present invention.

The rhodium carbonyl complex is, as characterized above, a rhodium containing compound in which the rhodium is complexed with CO. This can be achieved with just carbon monoxide or in addition to the carbon monoxide there may be included hydrogen and/or other organic or inorganic Lewis base materials to create the complex. In the last case, "complex" means a coordination compound formed by the union of one or more electronically rich molecules or atoms capable of independent existence with one or more electronically poor molecules or atoms, each of which is also capable of independent existence. The precise role of these Lewis bases in the practice of the present invention is not fully appreciated at present. They may be functioning as ligands and/or forming counter-ions under the reaction conditions of the present process or they may be functioning just merely as Lewis bases and neutralizing or tying up a molecular species which if allowed to remain "free" or in its non-based-bound state would adversely affect the productivity of the present invention.

Organic Lewis bases which are suitable in the practice of the present invention contain at least one Lewis base oxygen atom, said atoms possessing a pair of electrons available for the formation of coordinate bonds. In suitable embodiments the organic Lewis bases contain from 1 and upwards to 4 Lewis base atoms, preferably from 1 to 3 such atoms, and most preferably 1 or 2 Lewis base atoms. These organic Lewis bases are said to be multidentate or polydentate, that is to say, they are bidentate, tridentate, or quadridentate, depending on whether 2, 3 or 4 Lewis base atoms are involved.

Suitable organic nitrogen Lewis bases most generally contain carbon, hydrogen, and nitrogen atoms. Suitable organic oxygen Lewis bases most generally contain carbon, hydrogen, and oxygen atoms. Suitable organic aza-oxa Lewis bases most generally contain carbon, hydrogen, oxygen, and nitrogen atoms. The carbon atoms can be acyclic and/or cyclic such as aliphatic cycloaliphatic, aromatic (including fused and bridged) carbon atoms, and the like. Preferably, the organic Lewis bases contain from 2 to 60, most preferably 2 to 40 carbon atoms. The nitrogen atoms can be in the form of imino (—N=), amino (—N—), nitrillo (N≡), etc. Desirably, the Lewis base nitrogen atoms are in the form of imino nitrogen and/or amino nitrogen. The oxygen atoms can be in the form of groups such as hydroxyl (aliphatic or phenolic), carboxyl

carbonyloxy

oxy (—O—), carbonyl

etc., all of said groups containing Lewis base oxygen atoms. In this respect, it is the "hydroxyl" oxygen in the

group and the "oxy" oxygen in the

group that are the Lewis base atoms. The organic Lewis bases may also contain other atoms and/or groups such as alkyl, cycloalkyl, aryl, chloro, thiaalkyl, trialkylsilyl, and the like.

Illustrative organic oxygen Lewis bases include, by way of illustrations, glycolic acid, methoxyacetic acid, ethoxyacetic acid, diglycolic acid, thiodiglycolic acid, diethyl ether, tetrahydrofuran, dioxane, tetrahydropyran, pyrocatechol, citric acid, 2-methoxyethanol, 2-ethoxyethanol, 2-n-propoxyethanol, 2-n-butylethanol, 1,2,3-trihydroxybenzene, 1,2,4-trihydroxybenzene, 2,3-dihydroxynaphthalene, cyclohexane-1,2-diol, oxetane, 1,2-dimethoxybenzene, 1,2-diethoxybenzene, methyl acetate, ethanol, 1,2-dimethoxyethane, 1,2-diethoxyethane, 1,2-di-n-propoxyethane, 1,2-di-n-butoxyethane, pentane-2,4-dione, hexane-2,4-dione, heptane-3,5-dione, octane-2,4-dione, heptane-3,5-dione, octane-2,4-dione, 1-phenylbutane-1,3-dione, 3-methylpentane-2,4-dione; the mono- and dialkyl ethers of propylene glycol, of diethylene glycol, of dipropylene glycol; and the like.

Illustrative of the Lewis base nitrogen compounds suitable for use in the practice of the present invention are the aliphatic and aromatic primary, secondary and tertiary amines. This includes the mono-, di-, tri-, and polyamines and those compounds in which the Lewis base nitrogen forms part of a ring structure as in pyridine, quinoline, pyrimidine, morpholine, hexamethylenetetramine, their substituted derivatives, and the like. Also included are those compounds which contain both a Lewis base nitrogen atom and a Lewis base oxygen atom such as the alkanolamines, for example ethanolamine, diethanolamine, and the like; the various hydroxy substituted pyridines and the like. The use of these Lewis base nitrogen compounds in addition to the trialkanolamine borates, though operable in the present invention, do not represent a highly preferred mode of operation of the present invention.

Illustrative of the inorganic Lewis bases useful in the practice of the present invention are ammonia, hydroxides and halides, such as chloride, bromide, iodide, or fluoride; or mixtures thereof.

Any of the above Lewis bases may be provided to the reaction in compound form or as ligands which are in complex combination with the rhodium carbonyl compound initially charged to the reactor.

The precise role of the rhodium carbonyl complexes, such as the rhodium carbonyl clusters characterized previously, in the reaction of hydrogen with oxides of carbon to produce polyhydric alcohols is not fully appreciated at this time. Under the reaction conditions of the present process the carbonyl complexes are believed to be anionic in their active forms. Rhodium carbonyl anions are known to be involved in the following set of reactions as indicated by S. Martinengo and P. Chini, in Gazz. Chim. Ital., 102, 344 (1972) and the references cited therein.

The solubilization of the rhodium carbonyl complex is typically dependent upon the solvent used to effect the homogeneous mixture. The desired solvent is any liquid material which dissolves or keeps in solution the components of the homogeneous mixture taken from the reactor. It must be a solvent for the trialkanolamine borate, the reaction products and the rhodium carbonyl complex.

Illustrative solvents which are generally suitable in making the homogeneous mixture include, for example, ethers such as tetrahydrofuran, tetrahydropyran, diethyl ether, 1,2-dimethoxybenzene, 1,2-diethoxybenzene, the mono- and dialkyl ethers of ethylene glycol, of propylene glycol, of butylene glycol, of diethylene glycol, of dipropylene glycol, of triethylene glycol, of tetraethylene glycol, of dibutylene glycol, of oxyethyleneoxypropylene glycol, etc.; alkanols such as methanol, ethanol, propanol, isobutanol, 2-ethylhexanol, etc.; ketones such as acetone, methyl ethyl ketone, cyclohexanone, cyclopentanone, etc.; esters such as methyl acetate, ethyl acetate, propyl acetate, butyl

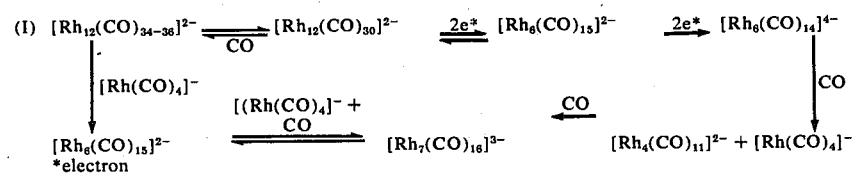

(I) $[Rh_{12}(CO)_{34-36}]^{2-} \underset{CO}{\rightleftharpoons} [Rh_{12}(CO)_{30}]^{2-} \xrightarrow{2e^*} [Rh_6(CO)_{15}]^{2-} \xrightarrow{2e^*} [Rh_6(CO)_{14}]^{4-}$ $[Rh(CO)_4]^-$ $[Rh_6(CO)_{15}]^{2-}$     $[(Rh(CO)_4]^- + CO$     $[Rh_7(CO)_{16}]^{3-}$     $[Rh_4(CO)_{11}]^{2-} + [Rh(CO)_4]^-$

*electron

Infrared spectra under reaction conditions of the present process have shown both the $Rh(CO)_4^-$ and $[Rh_{12}(CO)_{34-36}]^{2-}$ anions to be present at various concentrations at different times of the reaction. Therefore the set of reactions and equilibria shown in I above may represent the active rhodium carbonyl species responsible for polyhydric alcohol formation or may be merely symptomatic of some further intermediate transitory rhodium carbonyl structure which serves to convert the carbon monoxide and hydrogen to the polyhydric alcohol.

Assuming the active catalytic species is a rhodium carbonyl complex anion, or the formation of the active species under reaction conditions is directly dependent on the existence of these anions, allows one to better explain, in terms of reaction rates, productivity and catalyst stability, the role in solution the trialkanolamine borates, particularly triisopropanolamine borate, play in the reaction whereby hydrogen and an oxide of carbon are converted to the polyhydric alcohol. As reported by Hogen-Esch and Smid in the Journal of the American Chemical Society, 88, 307 (1966), triisopropanolamine borate induces the formation of solvent-separated from tight ion pairs. The trialkanolamine borates may enhance the reactivity of the rhodium carbonyl anions by minimizing any tendency these anions have to form "contact ion pairs" thereby producing a rhodium carbonyl anion having a higher reactivity in solution under the reaction conditions employed.

The reaction of the present invention is conducted in what is believed to be a homogeneous liquid phase, which means that the catalyst, the trialkanolamine borate and the reaction products formed from the reaction are in solution. Though the reaction to produce alcohols is essentially homogeneous there may be small amounts of insoluble catalyst particles depending upon the reaction conditions chosen.

acetate, methyl propionate, ethyl butyrate, methyl laurate, etc.; water; gamma-butyrolactone, delta-valerolactone; substituted and unsubstituted tetrahydrothiophene-1,1-dioxides (sulfolanes) as disclosed in U.S. application Ser. No. 537,885 filed on even date herewith, the disclosure at pages 6 and 7 of the specification of which is incorporated herein by reference; and others. The mono and dialkyl ethers of tetraethylene glycol, gamma-butyrolactone, particularly sulfolane and 3,4-bis(2-methoxyethoxy)sulfolane, are the preferred solvents.

The novel process is suitably effected over a wide superatmospheric pressure range of from about 800 psia to about 50,000 psia. Pressures as high as 50,000 psia and higher can be employed but with no apparent advantages attendant thereto which offset the unattractive plant investment outlay required for such high pressure equipment.

In one embodiment of this invention the upper pressure limitation is approximately 12,000 psia. Effecting the present process below about 12,000 psia, especially below about 8000 psia, and preferably at pressures below about 6000 psia, results in cost advantages which are associated with low pressure equipment requirements. A suitable pressure range for effecting the reaction is from about 1000 psia to about 12,000 psia, preferably from about 4000 to about 12,000 psia.

In a preferred embodiment of the present invention the pressures referred to above represent the total pressures of hydrogen and oxides of carbon in the reactor.

When practicing the present invention at pressures below about 12,000 psia the rate of desired product formation can be quite slow in certain solvents and in order to obtain a faster reaction rate there is provided to the reaction a promoter in the form of a salt. Suitable salts useful in the practice of the present invention include any organic or inorganic salt which does not adversely affect the production of polyhydric alcohols.

Illustrative of the salts useful in the practice of the present invention are the ammonium salts and the salts of the metals of Group I and Group II of the Periodic Table (Handbook of Chemistry and Physics - 50th Edition) for instance the halide, hydroxide, alkoxide, phenoxide and carboxylate salts such as sodium fluoride, cesium fluoride, cesium pyridinolate, cesium formate, cesium acetate, cesium benzoate, cesium p-methylsulfonyl benzoate ($CH_3SO_2C_6H_4COO$)Cs, rubidium acetate, magnesium acetate, strontium acetate, ammonium formate, ammonium benzoate and the like. Preferred are the cesium and ammonium carboxylate salts, most preferably their formate, benzoate and para-lower alkyl sulfonyl benzoate salts.

Also useful in the practice of the present invention are organic salts of the following formula:

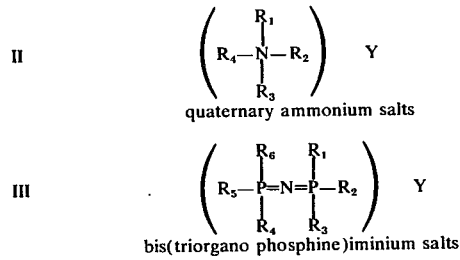

wherein $R_1$ through $R_6$ in formulas (II) and (III) above are any organic radicals which do not adversely affect the production of polyhydric alcohols by reacting oxides of carbon with hydrogen in the presence of the aforedefined rhodium carbonyl complex, such as a straight or branched chain alkyl group, having from 1 to 20 carbon atoms in the alkyl chain, such as methyl, ethyl, n-propyl, isopropyl, n-butyl, octyl, 2-ethylhexyl, dodecyl, and the like; or a cycloaliphatic group including the monocyclic and bicyclic groups cyclopentyl, cyclohexyl, and bicyclo[2.2.1] heptyl groups, and the like or an aryl, alkylaryl, or aralkyl group such as phenyl, naphthyl, xylyl, tolyl, t-butylphenyl, benzyl, beta-phenylethyl, 3-phenylpropyl and the like; or a functionally substituted alkyl such as beta-hydroxyethyl, ethoxymethyl, ethoxyethyl, phenoxyethyl, and the like; or a polyalkylene ether group of the formula $-(C_nH_{2n}O)_x-OR$ wherein $n$ has an average value from 1 to 4, $x$ has an average value from 2 to about 150, and R may be hydrogen or alkyl of 1 to about 12 carbon atoms. Illustrative of such polyalkylene ether groups are poly(oxyethylene), poly(oxypropylene), poly(oxyethyleneoxypropylene), poly(oxyethyleneoxybutylene), and the like. Y in formulas II and III above may be any anion which does not adversely affect the production of polyhydric alcohols in the practice of the present invention such as hydroxide; a halide, for instance fluoride, chloride, bromide and iodide; a carboxylate group, such as formate, acetate, propionate, and benzoate and the like; an alkoxide group such as methoxide, ethoxide, phenoxide, and the like; a functionally substituted alkoxide or phenoxide group such as methoxyethoxide, ethoxyethoxide, phenoxyethoxide and the like; a pyridinolate or quinolate group; and others. Preferably Y in formulas II and III, above, is a carboxylate, most preferably formate, acetate and benzoate.

A suitable method for preparing the bis(triorgano phosphine)iminium slats is disclosed in an article by Appel, R. and Hanas, A. appearing in Z. Anorg. u. Allg. Chem., 311, 290, (1961).

Other organic salts useful in the practice of the present invention include the quaternized heterocyclic amine salts such as the pyridinium, piperidinium, morpholinium, quinolinium salts and the like, e.g., N-ethylpyridinium fluoride, N-methylmorpholinium benzoate, N-phenylpiperidinium hydroxide, N,N'-dimethyl-2,2-bipyridinium acetate, and the like.

In one of the embodiments of the present invention, the anion of the above salt promoters may be any of the rhodium carbonyl anions. Suitable rhodium carbonyl anions include $[Rh_6(CO)_{15}]^{2-}$; $[Rh_6(CO)_{15}Y]^-$ wherein Y may be halogen, such as chlorine, bromine, or iodine, $[Rh_6(CO)_{15}(COOR'')]^-$ wherein R'' is lower alkyl or aryl such as methyl, ethyl, or phenyl; $[Rh_6(CO)_{14}]^{2-}$; $[Rh_7(CO)_{16}]^{3-}$; and $[Rh_{12}(CO)_{30}]^{2-}$.

Under reaction conditions where a salt promoter is employed the salt is desirably added with the initial charge of reactants in amounts of from about 0.5 to about 2.0 moles, preferably from about 0.8 to about 1.6 moles, and most preferably from about 0.9 to 1.4 moles of salt for every five atoms of rhodium present in the reaction mixture.

The trialkanolamine borate is used in amounts of at least about 0.1 mole of trialkanolamine borate for every one mole of rhodium present in the reaction mixture. Preferably the trialkanolamine borate is used in amounts of from about 0.5 mole to about 2 moles of trialkanolamine borate for about every one mole of rhodium present in the reaction mixture. Though amounts of the trialkanolamine borate outside this stated range may be used, no marked advantages have been observed.

The quantity of catalyst employed is not narrowly critical and can vary over a wide range. In general, the novel process is desirably conducted in the presence of a catalytically effective quantity of the active rhodium species which gives a suitable and reasonable reaction rate. Reaction proceeds when employed as little as about $1 \times 10^{-6}$ weight percent, and even lesser amounts of rhodium metal based on the total weight of reaction mixture. The upper concentration limit can be quite high, e.g., about 30 weight percent rhodium, and higher, and the realistic upper limit in practicing the invention appears to be dictated and controlled more by economics in view of the exceedingly high cost of rhodium metal and rhodium compounds. Depending on various factors such as the promoter of choice, the partial pressures of hydrogen and oxides of carbon, the total operative pressure of the system, the operative temperature, the choice of the organic co-diluent, and other considerations, a catalyst concentration of from about $1 \times 10^{-5}$ to about 5 weight percent rhodium (contained in the complex catalyst) based on the total weight of reaction mixture, is generally desirable in the practice of the invention.

The operative temperature which may be employed can vary over a wide range of elevated temperatures. In general, the novel process can be conducted at a temperature in the range of from about 100°C. and upwards to approximately 375°C., and higher. Operative temperatures outside this stated range, though not excluded from the scope of the invention, do not fall within certain desirable embodiments of the invention. At the lower end of the temperature range, and lower, the rate of reaction to desired product becomes markedly slow. At the upper temperature range, and beyond, signs of some catalyst instability are noted. Notwithstanding this factor, reaction continues and polyhydric alcohols and/or their derivatives are produced. Additionally, one should take notice of the equilibrium reaction for forming ethylene glycol:

$$2\ CO + 3H_2 \rightleftharpoons HOCH_2CH_2OH$$

At relatively high temperatures the equilibrium increasingly favors the left hand side of the equation. To drive the reaction to the formation of increased quantities of ethylene glycol, higher partial pressures of carbon monoxide and hydrogen are required. Processes based on correspondingly higher operative pressures, however, do not represent preferred embodiments of the invention in view of the high investment costs associated with erecting chemical plants which utilize high pressure utilities and the necessity of fabricating equipment capable of withstanding such enormous pressures. Suitable operative temperatures are between about 150°C. to about 300°C., and desirably from about 190°C. to about 275°C.

The novel process is effected for a period of time sufficient to produce the desired polyfunctional oxygen-containing products and/or derivatives thereof. In general, the residence time can vary from minutes to several hours, e.g., from a few minutes to approximately 24 hours, and longer. It is readily appreciated that the residence period will be influenced to a significant extent by the reaction temperature, the concentration and choice of the catalyst, the total gas pressure and the partial pressure exerted by its components, the concentration, and other factors. The synthesis of the desired product(s) by the reaction of hydrogen with an oxide of carbon is suitably conducted under operative conditions which give reasonable reaction rates and/or conversions.

The relative amounts of oxide of carbon and hydrogen which are initially present in the reaction mixture can be varied over a wide range. In general, the mole ratio of $CO:H_2$ is in the range of from about 20:1 to about 1:20, suitably from about 10:1 to about 1:10, and preferably from about 5:1 to about 1:5.

It is to be understood, however, that molar ratios outside the aforestated broad range may be employed. Substances or reaction mixtures which give rise to the formation of carbon monoxide and hydrogen under the reaction conditions may be employed instead of mixtures comprising carbon monoxide and hydrogen which are used in preferred embodiments in the practice of the invention. For instance, polyhydric alcohols are obtained by using mixtures containing carbon dioxide and hydrogen. Mixtures of carbon dioxide, carbon monoxide and hydrogen can also be employed. If desired, the reaction mixture can comprise steam and carbon monoxide.

The novel process can be executed in a batch, semicontinuous, or continuous fashion. The reaction can be conducted in a single reaction zone or a plurality of reaction zones, in series or in parallel, or it may be conducted intermittently or continuously in an elongated tubular zone or series of such zones. The material of construction should be such that it is inert during the reaction and the fabrication of the equipment should be able to withstand the reaction temperature and pressure. The reaction zone can be fitted with internal and/or external heat exchanger(s) to thus control undue temperature fluctuations, or to prevent any possible "run-away" reaction temperatures due to the exothermic nature of the reaction. In preferred embodiments of the invention, agitation means to vary the degree of mixing of the reaction mixture can be suitably employed. Mixing induced by vibration, shaker, stirrer, rotatory, oscillation, ultrasonic, etc., are all illustrative of the types of agitation means which are contemplated. Such means are available and well-known to the art. The catalyst may be initially introduced into the reaction zone batchwise, or it may be continuously or intermittently introduced into such zone during the course of the synthesis reaction. Means to introduce and/or adjust the reactants, either intermittently or continuously, into the reaction zone during the course of the reaction can be conveniently utilized in the novel process especially to maintain the desired molar ratios of and the partial pressures exerted by the reactants.

As intimated previously, the operative conditions can be adjusted to optimize the conversion of the desired product and/or the economics of the novel process. In a continuous process, for instance, when it is preferred to operate at relatively low conversions, it is generally desirable to recirculate unreacted synthesis gas with/without make-up carbon monoxide and hydrogen to the reaction. Recovery of the desired product can be achieved by methods well-known in the art such as by distillation, fractionation, extraction, and the like. A fraction comprising rhodium catalyst, generally contained in byproducts and/or normally liquid organic diluent, can be recycled to the reaction zone, if desired. All or a portion of such fraction can be removed for recovery of the rhodium values or regeneration to the active catalyst and intermittently added to the recycle stream or directly to the reaction zone.

The active forms of the rhodium carbonyl clusters may be prepared by various techniques. They can be preformed and then introduced into the reaction zone. Alternatively, any of the host of rhodium-containing substances as well as any of the low pressure promoters illustrated previously can be employed in lieu of tetrarhodium dodecacarbonyl. The organic Lewis bases or other promoters such as the aforedefined low pressure salt promoters, can also be added thereto. The rhodium carbonyl complex or cluster forming reaction can be effected under a carbon monoxide pressure, with or without $H_2$, of about 1 to 15 atmospheres, and higher, using a temperature of about 30°C to about 100°C for a period of time ranging from minutes to a few days, generally from about 30 minutes to about 24 hours. The resulting rhodium carbonyl complex contained in the solvent is catalytically active in this process. In preparing the aforesaid complexes, one can suitably employ from about 0.01 to about 25 moles salt or Lewis base nitrogen promoter per mole of rhodium (contained in the rhodium compound used as a rhodium source). Ratios outside this stated range can be employed especially when it is desirable to use diluent quantities of the promoters.

The equipment arrangement and procedure which provides the capability for determining the existence of anionic rhodium carbonyl complexes or clusters having defined infrared spectrum characteristics, during the course of the manufacture of polyhydric alcohols from carbon monoxide and hydrogen, pursuant to this invention is disclosed and schematically depicted in U.S. Patent application Ser. No. 462,109, filed Apr. 18, 1974, the disclosure of which is incorporated herein by reference.

A particularly desirable infrared cell construction is described in copending U.S. Patent application, Ser. No. 451,437, filed Mar. 15, 1974, and its disclosure of a preferred cell construction is incorporated herein by reference.

The "oxide of carbon" as covered by the claims and as used herein is intended to mean carbon monoxide and mixtures of carbon dioxide and carbon monoxide, either introduced as such or formed in the reaction. Preferably, the oxide of carbon is carbon monoxide.

The following examples are merely illustative and are not presented as a definition of the limits of the invention.

EXAMPLE 1

A 150 ml. capacity stainless steel reactor capable of withstanding pressures up to 7,000 atmospheres was charged with a premix of 75 cubic centimeters (cc) of sulfolane, 3.0 millimoles (mmol), 0.77 grams, of rhodium dicarbonylacetylacetonate, and 0.63 mmol. of triisopropanolamine borate. The reactor was sealed and charged with a gaseous mixture, containing equal molar amounts of carbon monoxide and hydrogen, to a pressure of 8,000 pounds per square inch (psig). Heat was applied to the reactor and its contents; when the temperature of the mixture inside the reactor reached 190°C., as measured by a suitably placed thermocouple, an additional adjustment of carbon monoxide and hydrogen ($H_2$:CO=1:1 mole ratio) was made to bring the pressure back to 8000 psig. The temperature was maintained at 220°C for 4 hours. During this period of time additional carbon monoxide and hydrogen was added whenever the pressure inside the reactor dropped below about 7500 psig. With these added repressurizations the pressure inside the reactor was maintained at 8000 psig ± 400 psig over the entire 4 hour period.

After the 4 hour period, the vessel and its contents were cooled to room temperature, the excess gas vented and the reaction product mixture was removed. Analysis of the reaction product mixture was made by gas chromatographic analysis using a Hewlett Packard FM model 810 Research Chromatograph.

Analysis of the product mixture showed 1.67 grams of ethylene glycol, 1.78 grams of methanol, and a rhodium recovery of 86 percent (80% + 6% in wash) based on the total rhodium charged to the reactor.

Rhodium recovery was determined by atomic absorption analysis of the contents of the reactor after the venting of the unreacted gases at the end of the reaction. A further analysis was run on a "wash" of the reactor and the results of the two analysis were combined and reported as the rhodium recovered. The wash of the reactor consisted of charging to the reactor 100 cc of the solvent used for that experiment, and bringing the reactor and its contents to a temperature of 160°C and a pressure of 14,000 to 15,000 psig and maintaining these conditions for a period of 30 minutes. The reactor was then cooled and the unreacted gases vented and an atomic absorption analysis for rhodium was run on the reactor's contents. The rhodium recovery values therefore would be the percent rhodium based on the total rhodium charged to the reactor that is soluble or suspended in the reaction mixture and the wash after the specified reaction time.

The same equipment and procedure used in Example 1 were used in all the examples in Tables I through VI except for the reactants and conditions specified. The product weights in Tables I–VI are reported in grams.

TABLE I

TRIISOPROPANOLAMINE BORATE IN SULFOLANE[a]

| Example | °C Temperature | Borate, mmoles | MeOH, g | Glycol, g | Rh Recovered, % |
|---|---|---|---|---|---|
| 1 | 220° | 0.63 | 1.78 | 1.67 | 80 + 6 |
| 2 | 240° |  | 2.41 | 3.75 | 74 + 6 |
| 3 | 240° | 1.25 | 3.30 | 5.35 | 82 + 8 |
| 4 | 220° | 2.5 | 1.96 | 2.99 | 77 + 7 |
| 5 | 240° |  | 3.26 | 5.29 | 62 + 6 |
| 6 | 260° |  | 5.17 | 6.52 | 63 + 6 |
| 7 | 270° |  | 2.00 | 1.50 | 57 + 5 |
| 8 | 220° | 5.0 | 2.00 | 2.89 | 79 + 7 |
| 9 | 270° |  | 5.19 | 4.94 | 64 + 4 |

[a]1/1 $H_2$/CO, 8000 psig, 4 hr., 3.0 mmoles Rh(CO)$_2$acac, 75 ml sulfolane.

TABLE II

TRIISOPROPANOLAMINE BORATE/HCO$_2$Cs IN SULFOLANE[a]

| Example | Temp. | Borate mmoles | HCO$_2$Cs, mmole | MeOH, g | Glycol, g | Rh Recovered, % |
|---|---|---|---|---|---|---|
| 10 | 220° | 1.25 | 0.50 | 2.07 | 3.26 | 87 + 9 |
| 11 | 220° | 2.5 | 0.50 | 2.40 | 3.33 | 85 + 8 |
| 12 | 220° | 5.0 | 0.50 | 2.69 | 3.45 | 84 + 5 |
| 13 | 240° | 0 | 0.50 | 4.07 | 1.50 | 72 + 5 |
| 14 | 240° | 2.5 | 0.50 | 4.19 | 5.65 | 77 + 3 |
| 15 | 250° | 0 | 0.65 | 4.40 | 4.70 | 65 + 18 |
| 16 | 250° | 2.5 | 0.65 | 4.44 | 6.03 | 80 + 5 |
| 17 | 260° | 2.5 | 0.65 | 4.50 | 6.00 | 77 + 10 |
| 18 | 260° | 5.0 | 0.65 | 4.61 | 6.50 | 80 + 9 |
| 19 | 240° | 2.5 | 0.65 | 4.37 | 6.09 | 84 + 4 |
| 20 | 240° | 2.5 | 0.75 | 4.68 | 5.39 | 79 + 5 |
| 21 | 240° | 2.5 | 0.875 | 4.31 | 5.65 | 79 + 4 |
| 22 | 270° | 2.5 | 0.65 | 4.35 | 4.50 | 57 + 7 |

TABLE II-continued

TRIISOPROPANOLAMINE BORATE/HCO₂Cs IN SULFOLANE[a]

| Example | Temp. | Borate mmoles | HCO₂Cs, mmole | MeOH, g | Glycol, g | Rh Recovered, % |
|---|---|---|---|---|---|---|
| 23 | 280° | 2.5 | 0.65 | 4.15 | 2.85 | 49 + 12 |

[a] 1/1 $H_2$/CO, 8000 psig, 4 hr., 3.0 mmoles Rh(CO)₂acac, 75 ml sulfolane.

TABLE III

TRIETHANOLAMINE BORATE (TEAB) IN SULFOLANE[a]

| Example | Borate, mmoles | °C Temp. | MeOH, g | Glycol, g | Rh Recovered, % |
|---|---|---|---|---|---|
| 24 | TEAB, 2.5 | 220° | 2.33 | 2.22 | 84 + 5 |
| 25 | TEAB, 5.0 | 220° | 2.03 | 1.82 | 74 + 7 |
| 26 | TEAB, 2.5 | 240° | 3.71 | 4.91 | 86 + 5 |
| 27 | TEAB, 2.5 | 250° | 3.60 | 4.90 | 80 + 9 |

[a] 1/1 $H_2$/CO, 8000 psig, 4 hr, 3.0 mmoles Rh(CO)₂acac, 75 ml sulfolane, 0.65 mmole HCO₂Cs.

TABLE V

TRIISOPROPANOLAMINE BORATE IN TETRAGLYME[a]

| Example | Temperature | Salt, mmole | Borate, mmoles | MeOH, g | Glycol, g | Rh Recovered, % |
|---|---|---|---|---|---|---|
| 36 | 220° | PhCO₂Cs[b], 0.65 mmole | 0 | 1.82, 1.44[e] | 4.21, 4.25[e] | 75 + 6, 81 + 13[e] |
|  |  |  | 2.5 | 1.80 | 4.00 | 85 + 8 |
| 37 | 230° | PhCO₂Cs, 0.65 mmole | 0 | 2.15 | 3.48 | 63 + 24 |
|  |  |  | 2.5 | 3.90 | 5.05 | 78 + 21 |
| 38 | 240° | PhCO₂Cs, 0.65 mmole | 0 | 2.15 | 2.90 | 27 + 52 |
|  |  |  | 2.5 | 3.23 | 5.67 | 61 + 31 |
|  |  |  | 5.0 | 2.43 | 4.08 | 32 + 58 |
| 39 | 220° | NH₄OAc[c], 0.65 mmole | 0 | 1.45 | 0.50 | 55 + 26 |
|  |  |  | 2.5 | 1.15 | 0.50 | 55 + 24 |
| 40 | 220° | PhCO₂NH₄[d], 0.65 mmole | 0 | 1.24 | 0.63 | 49 + 38 |
|  |  |  | 2.5 | 1.70 | 0.60 | 72 + 25 |

[a] 1/1 $H_2$/CO, 8000 psig, 4 hr, 3.0 mmoles Rh(CO)₂acac, 75 ml tetraglyme.
[b] cesium benzoate
[c] ammonium acetate
[d] ammonium benzoate
[e] duplicate experiments

TABLE IV

MISCELLANEOUS CO-PROMOTERS AND TRIISOPROPANOLAMINE BORATE IN SULFOLANE[a]

| Example | Co-Promoter, mmoles | Borate, mmoles | MeOH, g | Glycol, g | Rh Recovered, % |
|---|---|---|---|---|---|
| 28 | — | 2.5 | 5.17 | 6.52 | 63 + 6 |
| 29 | HCO₂Cs[b], 0.5 |  | 6.47 | 6.40 | 79 + 5 |
| 30 | Ph₃SiH[c], 0.5 |  | 3.52 | 4.40 | 57 + 5 |
| 31 | 5.0 |  | 3.76 | 4.80 | 63 + ? |
| 32 | HCO₂Cs, 0.65 | 5.0 | 4.61 | 6.50 | 80 + 9 |
| 33 | CH₃CO₂NH₄[d], 0.65 |  | 4.46 | 5.55 | 78 + 5 |
| 34 | PhCO₂NH₄[e], 0.65 |  | 4.75 | 6.00 | 80 + 5 |
| 35 | NH₄O₂CCO₂NH₄, 0.65 |  | 3.64 | 4.90 | 62 + ? |

[a] 1/1 $H_2$/CO, 8000 psig, 4 hr, 3.0 mmoles Rh(CO)₂acac, 75 ml sulfolane, 260°C
[b] cesium formate
[c] triphenyl silane
[d] ammonium acetate
[e] ammonium benzoate

TABLE VI

TRIISOPROPANOLAMINE BORATE IN MIXED SOLVENTS[a]

| Example | Solvent (v/v) | MeOH, g | Glycol, g | Rh Recovered, % |
|---|---|---|---|---|
| 41 | Tetraglyme (75/0) | 3.23 | 5.67 | 61 + 31 |
| 42 | Tetraglyme/butyrolactone (65/10) | 3.20 | 6.00 | 75 + 9 |
| 43 | Tetraglyme/water (65/10) | 3.54 | 4.28 | 28 + 41 |
| 44 | Tetraglyme/tetrahydrofuran (65/10) | 3.23 | 5.20 | 61 + 32 |
| 45 | Tetraglyme/sulfolane (65/10) | 4.01 | 6.40 | 73 + 15 |
| 46 | Tetraglyme/acetone (65/10) | 3.00 | 4.30 | 47 + 40 |

[a] 1/1 $H_2$/CO, 8000 psig, 4 hr, 3.0 mmoles Rh(CO)₂acac, 2.5 mmoles triisopropanolamine borate, 0.65 mmole PhCO₂Cs, 240°.

What is claimed is:

1. The process of making alkane diols and triols having from 2 to 3 carbon atoms in the molecule which comprises reacting in a homogeneous liquid phase mixture of hydrogen and oxides of carbon in the presence of a rhodium carbonyl complex and a trialkanolamine borate at a pressure of from about 1000 psia to about 50,000 psia correlated with a temperature of about 100°C to about 375°C sufficient to produce said diols and triols.

2. The process of claim 1 wherein the temperature is from about 150°C to about 300°C.

3. The process of claim 2 wherein the temperature is from about 190°C to about 275°C.

4. The process of claim 2 wherein the reaction is effected in the presence of an organic solvent.

5. The process of claim 4 wherein the trialkanolamine borate has the formula $N(OR)_3B$ wherein R is a straight or branched chain alkylene radical having from 2 to 14 carbon atoms in the radical.

6. The process of claim 5 wherein the solvent is sulfolane.

7. The process of claim 6 wherein the trialkanolamine borate is triisopropanolamine borate.

8. The process of claim 5 wherein the reaction is effected in the presence of a salt.

9. The process of claim 8 wherein the salt is at least one of Group I metal, Group II metal, ammonium and bis(triorganophosphine)iminium salts.

10. The process of claim 9 wherein the solvent is sulfolane.

11. The process of claim 9 wherein the solvent in the dimethyl ether of tetraethylene glycol.

12. The process of claim 9 wherein the salt is cesium formate.

13. The process of claim 9 wherein the salt is cesium benzoate.

14. The process of claim 9 wherein the salt is ammonium acetate.

* * * * *